United States Patent
Saiki et al.

(10) Patent No.: US 8,039,561 B2
(45) Date of Patent: Oct. 18, 2011

(54) METHOD FOR THE PREPARATION OF A SILICON-CONTAINING POLYSULFIDE-TYPE POLYMER

(75) Inventors: Takeaki Saiki, Hokkaido (JP); Makoto Iwai, Chiba Prefecture (JP)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 380 days.

(21) Appl. No.: 10/533,169

(22) PCT Filed: Oct. 28, 2003

(86) PCT No.: PCT/JP03/13800
§ 371 (c)(1),
(2), (4) Date: Apr. 17, 2006

(87) PCT Pub. No.: WO2004/039867
PCT Pub. Date: May 13, 2004

(65) Prior Publication Data
US 2006/0235120 A1    Oct. 19, 2006

(30) Foreign Application Priority Data
Oct. 31, 2002 (JP) ................. 2002-318262

(51) Int. Cl.
C08F 283/00 (2006.01)
C08F 283/06 (2006.01)
C08G 75/04 (2006.01)
C08L 81/02 (2006.01)
C08G 77/60 (2006.01)

(52) U.S. Cl. .............. 525/536; 528/23; 528/25; 528/32

(58) Field of Classification Search .................... 525/535
See application file for complete search history.

(56) References Cited

U.S. PATENT DOCUMENTS

| 3,317,461 | A |   | 5/1967  | Plueddemann |         |
|-----------|---|---|---------|-------------|---------|
| 3,476,826 | A | * | 11/1969 | Millen      | 528/25  |
| 3,574,766 | A | * | 4/1971  | Meyer et al.| 568/41  |
| 3,872,059 | A | * | 3/1975  | Ely         | 528/17  |
| 3,925,331 | A | * | 12/1975 | Ely         | 528/25  |
| 3,946,059 | A |   | 3/1976  | Janssen et al. |      |
| 4,000,347 | A | * | 12/1976 | Ranney et al. | 428/419 |
| 4,020,043 | A | * | 4/1977  | Siefken     | 528/23  |
| 4,096,131 | A | * | 6/1978  | Price et al. | 528/30 |
| 5,827,912 | A |   | 10/1998 | Scholl      |         |
| 5,914,364 | A | * | 6/1999  | Cohen et al. | 524/494 |
| 6,147,147 | A | * | 11/2000 | Hoover et al. | 524/175 |
| 6,359,046 | B1 |  | 3/2002  | Cruse       |         |
| 6,416,869 | B1 | * | 7/2002 | van Ooij et al. | 428/450 |
| 6,527,022 | B2 | * | 3/2003 | Visel et al. | 152/209.1 |
| 6,955,728 | B1 | * | 10/2005 | van Ooij et al. | 148/240 |
| 7,138,537 | B2 | * | 11/2006 | Cruse et al. | 556/457 |
| 7,351,759 | B2 | * | 4/2008  | Araujo-Da-Silva et al. | 524/262 |
| 2003/0114601 | A1 | * | 6/2003 | Cruse et al. | 525/332.6 |

FOREIGN PATENT DOCUMENTS

| CA | 908030 A | * | 8/1972 |
| CH | 493584 |   | 6/1964 |
| GB | 1 457 872 |  | 12/1976 |
| JP | 9-3248 |   | 1/1997 |
| JP | 10-120788 | | 5/1998 |
| JP | 10-139939 | | 5/1998 |
| JP | 2000-63521 | | 2/2000 |

OTHER PUBLICATIONS

Leslie R. Dix, John R. Ebdon, Philip Hodge, Chain extension and crosslinking of telechelic oligomers—II. Michael additions of bisthiols to bismaleimides, bismaleates and bis(acetylene ketone)s to give linear and crosslinked polymers, European Polymer Journal Vol. 31, Issue 7, , Jul. 1995, pp. 653-658. (http://www.sciencedirect.com/science/artic.*

Yangxing Li et al. Crosslinkable fumed silica-based nanocomposite electrolytes for rechargeable lithium batteries. Department of Chemical & Biomolecular Engineering, North Carolina State University, Raleigh, NC 27695-7905, USA. Journal of Power Sources 161 (2006) 1288-1296.*

English language Abstract for JP 10-120788 extracted from espacenet.com database dated Sep. 20, 2005.

English language Abstract for JP 10-139939 extracted from espacenet.com database dated Sep. 20, 2005.

English language Abstract for JP 2000-63521 extracted from espacenet.com database dated Sep. 20, 2005.

* cited by examiner

*Primary Examiner* — Randy Gulakowski
*Assistant Examiner* — Mike M Dollinger
(74) *Attorney, Agent, or Firm* — Howard & Howard Attorneys PLLC

(57) ABSTRACT

To provide a highly efficient and stable method for the preparation of a silicon-containing polysulfide-type polymer, in particular, a polysulfide-type polymer with organosilyl groups, the method being carried out without generation of by-products that could have high impact on the environment. A method for the preparation of a silicon-containing polysulfide-type polymer characterized by mixing (A) a silicon-containing compound having a silicon atom-bonded monovalent organic group having an aliphatic unsaturated bond; (B) a polysulfide polymer with at least two mercapto groups in one molecule; and (C) an organic base or ammonia; the mixing being carried out in the presence of (D) sulfur.

13 Claims, No Drawings

METHOD FOR THE PREPARATION OF A SILICON-CONTAINING POLYSULFIDE-TYPE POLYMER

TECHNICAL FIELD

The present invention relates to a method for the preparation of silicon-containing polysulfide-type polymers, in particular, polysulfide-type polymers that contain organosilyl groups. More specifically, the invention relates to a highly efficient and stable method for the preparation of silicon-containing polysulfide-type polymers, in particular, polysulfide-type polymers that contain organosilyl groups, the method being carried out without generation of by-products that could have high impact on the environment.

BACKGROUND ART

It is known in the art that a silicon-containing polysulfide polymer which contains in its molecule repeating units represented by the formula $(S_zR^9)_k$ (where "z" is a number greater than and equal to 1, $R^9$ is a divalent organic group, and "k" is a number greater than and equal to 1 is used as an additive that improves properties of a dyene-type rubber composition for molding tires, rubber rolls, or similar products. For example, Japanese Patent Application Publication (hereinafter referred to as Kokai) H9-3248 (equivalent to U.S. Pat. No. 5,827,912) describes synthesis of a silylated polysulfide polymer from a mercaptosilane, dithiol, and sulfur dichloride in the presence of a non-aqueous solvent, as well as synthesis of a silylated polysulfide from a silylated halogenated alkyl, dihalogenated alkyl, and a metal sulfide in the presence of a non-aqueous solvent. However, these methods are associated with a number of problems such as generation of a toxic gaseous hydrochloride, conduction of reactions under completely anhydrous conditions, consumption of large quantities of solvents, and difficulties in connection with separation of the by-product metal halides, due to increasing viscosity of the product.

Furthermore, Kokai H10-120788 and Kokai H10-139939 describe synthesis of silyl-capped polysulfide polymers through an addition reaction between a mercapto-capped polysulfide polymer and an epoxysilane and synthesis of a silyl-capped polysulfide through an addition reaction between a polysulfide polymer end-capped with hydroxyl groups and an isocyanate silane. However, the addition reaction between the mercapto-capped polysulfide polymer and an epoxysilane is accompanied by gelation caused by hydroxyl groups, which are formed after the addition reaction between the mercapto groups and epoxy groups. Another unfavorable factor is that the above processes have low efficiency as they require a two-stage reaction that requires addition of sulfur in the presence of an alkali catalyst after introduction of alkoxysilyl groups resulting from the aforementioned addition reaction and adjustment of a sulfur number in sulfide groups. On the other hand, the addition reaction between the isocyanate silane and the polysulfide polymer having molecular terminals capped with hydroxyl groups also encounters a number of problems. These problems are the following: instability caused by a concurrent condensation reaction that occurs simultaneously with the addition reaction between the hydroxyl groups on the terminals of the polysulfide polymer and alkoxy groups contained in the isocyanate silane; high cost of the isocyanate silane; and low reaction efficiency resulting from the necessity of using the same adjustment of the sulfur number as in the addition reaction after introduction of alkoxysilyl groups generated, in this case, in the aforementioned condensation reaction.

Kokai 2000-63521 discloses synthesis of a polysulfide polymer end-capped with silyl groups by causing an addition reaction between a vinyl silane and a polysulfide polymer having on its molecular terminals mercapto or hydroxyl groups. The problem associated with this method is that the process has low efficiency as it requires a two-stage reaction with addition of sulfur in the presence of an alkali catalyst after introduction of silyl groups resulting from the aforementioned addition reaction between the vinyl silane and polysulfide polymer with subsequent adjustment of sulfur number in sulfide groups.

DISCLOSURE INVENTION

As a result of study aimed at the solution of the above problems, the authors arrived at the present invention. More specifically, it is an object of the present invention to provide a highly efficient and stable method for the preparation of a silicon-containing polysulfide-type polymer, in particular, a polysulfide-type polymer that contains organosilyl groups, the method being carried out without generation of by-products that could have high impact on the environment.

The invention relates to a method for the preparation of a silicon-containing polysulfide-type polymer characterized by mixing (A) a silicon-containing compound having a silicon atom-bonded monovalent organic group with an aliphatic unsaturated bond; (B) a polysulfide polymer with at least two mercapto groups in one molecule; and (C) an organic base or ammonia; the mixing being carried out in the presence of (D) sulfur.

BEST MODE FOR CARRYING OUT THE INVENTION

The invention will now be described in more detail. Let us first consider components, which in the method of the invention form starting materials.

Component (A) is a silicon-containing compound having a silicon atom-bonded monovalent organic group with an aliphatic unsaturated bond. Preferably, this component is an organosilane expressed by the following formula (1):

group with 1 to 10 carbon atoms. Preferably, the aforementioned monovalent hydrocarbon group is an alkyl group, aryl group, or an aralkyl group. Alkyl groups that represent $R^1$ can be exemplified by methyl, ethyl, propyl, octyl, decyl, hexadecyl, and octadecyl groups. Aryl groups that represent $R^1$ can be exemplified by phenyl, tolyl, and xylyl groups. Aralkyl groups that represent $R^1$ can be exemplified by benzyl group or phenethyl group. Alkoxyalkylene groups that represent $R^1$ can be exemplified by methoxyethylene, ethoxyethylene, or ethoxypropylene groups. Most preferable of the above for $R^1$ are methyl or ethyl groups. In the aforementioned formula, $R^2$ is a monovalent hydrocarbon group with 1 to 15 carbon atoms, other than the one having aliphatic unsaturated bond. This may be an alkyl, aryl, aralkyl, or a halogenated alkyl groups. Alkyl groups that represent $R^2$ can be exemplified by methyl, ethyl, propyl, octyl, decyl, hexadecyl, and octadecyl groups. Aryl groups that represent $R^2$ can be exemplified by phenyl, tolyl, and xylyl groups. Aralkyl groups that represent $R^2$ can be exemplified by benzyl group or phenethyl group, and halogenated alkyl groups that represent $R^2$ can be exemplified by 3,3,3-trifluoropropyl group and perfluorooctylethyl group. Most preferable of the above for $R^2$ are alkyl groups and aryl groups. In the above formula, $R^5$ is a monovalent hydrocarbon group with 2 to 16 carbon atoms having an aliphatic unsaturated bond. Preferably, these groups are alkenyl groups, aryl-substituted alkenyl groups, acryloxyalkyl groups, or methacryloxyalkyl groups. Alkenyl groups that represent $R^5$ can be exemplified by vinyl group, allyl group, 5-hexenyl group, 4-hexenyl group, or 3-hexenyl group. Aryl-substituted alkenyl groups that represent $R^5$ may comprise styryl group. Acryloxyalkyl groups of $R^5$ can be represented by acryloxypropyl group, and methacryloxyalkyl group of $R^5$ can be represented by methacryloxypropyl group. Most preferable for $R^5$ are alkenyl groups, acryloxyalkyl groups, and methacryloxyalkyl groups. Vinyl group and methacryloxypropyl group can be recommended as well. If necessary, the aforementioned monovalent hydrocarbon groups with an aliphatic unsaturated bond can be used in combinations. In the above formula, "a" is an integer between 0 and 3, preferably between 0 and 2.

Component (A) can be represented by the following compounds or combinations thereof: vinyltrimethoxysilane, vinyltriethoxysilane, vinyltrimethoxyethoxysilane, vinylmethyldimethoxysilane, vinylmethyldiethoxysilane, vinyltrimethylsilane, vinyltriethylsilane, vinyl3,3,3-trifuluoropropyldimethoxysilane, 5-hexenyltrimethoxysilane, 3-acryloxypropyltrimethoxysilane, and 3-methacryloxypropyltrimethoxysilane.

Component (B) is a polysulfide polymer having molecular terminals capped with mercapto groups, which is expressed by the following formula (2):

$$HSR^3(S_yR^3)_nSH \qquad (2).$$

Component (B) is a liquid substance preferably with a viscosity of 0.1 to 1000 Pa·s at 25° C. and with a weight-average molecular weight within the range of 100 to 20000. This component has an essentially linear molecular structure but may have a partially-branched linear structure as well. In the above formulae, $R^3$ is selected from an alkylene group with 2 to 10 carbon atoms, an arylene group with 6 to 10 carbon atoms, an alkylenoxyalkylene group with 2 to 10 carbon atoms, or a divalent organic group of formula (3):

$$—R^8(OR^8)_m— \qquad (3)$$

(where $R^8$ are the same or different alkylene groups with 1 to 10 carbon atoms, and "m" is an integer between 2 and 20, preferably between 2 and 4), or a hydroxy-substituted alkylene group with 3 to 12 carbon atoms. The alkylene group that represents $R^3$ can be exemplified by a methylene, ethylene, propylene, and butylene group. The arylene group that represents $R^3$ can be exemplified by a phenylene, benzylene, and methylbenzylene group, while the alkyleneoxyalkylene group that represents $R^3$ can be exemplified by a methyleneoxymethylene, ethylenoxyethylene, and propylenoxypropylene. Examples of organic groups that may represent formula (3) of $R^3$ can be represented by the following formulae:
—CH$_2$OCH$_2$OCH$_2$—
—C$_2$H$_4$OCH$_2$OC$_2$H$_4$—
—C$_2$H$_4$OC$_2$H$_4$OC$_2$H$_4$—
—C$_3$H$_6$OCH$_2$OC$_3$H$_6$—
—C$_2$H$_4$OC$_2$H$_4$OC$_2$H$_4$OC2H$_4$—.
The hydroxy-substituted alkylene group of $R^3$ can be represented by the following formulae:
—CH$_2$CH(OH)CH$_2$—
—C$_2$H$_4$CH(OH)C$_2$H$_4$—.
The most preferable divalent organic group is the one expressed by the following formula:
—C$_2$H$_4$OCH$_2$OC$_2$H$_4$—.
The aforementioned divalent organic groups can be used in combinations of two or more. Furthermore, in the above formulae (2), "y" is a number with a mean value between 1.7 and 2, and "n" is a number with a mean value between 1 and 120, preferably, between 5 and 60.

Component (B) can be prepared by the methods disclosed in U.S. Pat. No. 2,366,963 issued to Patrick and in Kokai H$_4$-363325.

It is recommended to use component (B) in an amount of 10 to 200 mole %, preferably 40 to 50 mole % relative to component (A). If component (B) is used in an amount below the recommended lower limit, component (A) will become in excess, and the process will be inefficient. If, on the other hand, component (B) is used in an amount exceeding the recommended upper limit, this will result in the formation of unreacted mercapto groups and lead to increase in viscosity.

Component (C) is an organic base or ammonia. The organic base can be exemplified by aliphatic amines, monoarylamines, tertiary ammonium hydroxides, sulfonium bases, and nitrogen-containing cyclic organic bases. Component (C) functions as a catalyst for an addition reaction which is carried out between components (A) and (B) in the presence of below-described sulfur as component (D), and at the same time as a catalyst for adjusting the sulfur bond number in the molecule.

Component (C) can be represented by the following compounds: ammonia; trimethylamine, triethylamine, tripropylamine, trioctylamine, or similar aliphatic amines; aniline, N,N'-dimethylaniline, or similar monoarylamines; pyridine, quinoline, piperidine, or similar nitrogen-containing cyclic organic bases, or mixtures of the above. Of these, most preferable are aliphatic amines, tertiary aliphatic amines, and, especially, triethylamine.

Component (C) should be used in an amount of 0.01 to 10 mole %, preferably, 0.1 to 10 mole % relative to component (A). If it is used in an amount below the recommended lower limit, the reaction will not have a sufficient progress. If, on the other hand, component (C) is used in an amount exceeding the recommended upper limit, the process will become inefficient.

Component (D) is sulfur. This component works in conjunctions with component (C) and is required for both the addition reaction between components (A) and (B) and for adjusting the sulfur bond number in the molecule. If component (D) were not used and component (C) were used alone, the addition reaction between components (A) and (B) would not properly progress. Although there are no special restrictions with regard to the type of component (D) suitable for the invention, it is recommended to use dehydrated sulfur. It is also recommended to utilize sulfur in the form of powder or flakes.

It is recommended that component (D) be added in such an amount that sulfur atoms constitute 1 to 600 mole %, preferably 1 to 300 mole %, and even more preferably 10 to 200 mole %, relative to 1 mole of the repeating units ($S_yR^3$) in component (B). More specifically, for silicon-containing polysulfide-type polymers of the invention, in particular polysulfide-type polymers with organosilyl groups having tetrasulfide structures, such as those having 4 sulfur atoms in the repeating units, sulfur should be used in an amount of 200 mole % per 1 mole of the repeating units of component (A). Similarly, for trisulfide structures sulfur should be used in an amount of 100 mole %, and for disulfide structure in an amount of 10 to 30 mole % per 1 mole of the repeating units of component (A).

The following description relates to preparation conditions in accordance with the method of the invention.

The silicon-containing polysulfide-type polymer of the invention, in particular, the polysulfide-type polymer that contains organosilyl groups is prepared by uniformly mixing components (A) to (D), and then a reaction is carried out, preferably in an atmosphere of inert gas and at a temperature within the range between room temperature and 200° C., preferably between 40 and 110° C., and even more preferably between 60 and 95° C. If the reaction is carried out at a temperature below the recommended lower limit, the reaction will not properly progress. If, on the other hand, the reaction temperature exceeds the recommended upper limit, the aforementioned silicon-containing polysulfide-type polymer, in particular, the polysulfide-type polymer that contains organosilyl groups can be decomposed. It is recommended that the reaction be carried out during 10 min. to 9 hours, preferably 1 to 3 hours. From an economical point of view, it is recommended to use nitrogen gas as an appropriate inert gas. In order to prevent a very rapid growth of the reaction heat, it is recommended to add component (D) in a divided amount at the reaction temperature while mixing components (A) through (C).

In accordance with the method of the invention, the reaction can be carried out in a solvent. Although there are no special restrictions with regard to the type of the solvent, it is preferable to select the one with high solubility of component (B). The recommended solvents are the following: benzene, toluene, xylene, or similar aromatic solvents. If component (A) is an alkoxysilane and the solvent is an alcohol, it is recommended to use an alcohol that has the same groups as the silicon-bonded alkoxy groups. If the alcohol used has different groups, the alkoxy groups will cause an exchange reaction, and a substance with a mixture of alkoxy groups of two types will be formed. However, an intentional use of alkoxy groups of two different types is quite possible.

If necessary, after the reaction is completed, the non-reacted starting material is removed from the reaction product by heating it in vacuum, whereby a target product is obtained in the form of a silicon-containing polysulfide-type polymer, in particular, in the form of a polysulfide-type polymer that contains organosilyl groups. It is recommended that the obtained silicon-containing polysulfide-type polymer comprise a polysulfide-type polymer with organosilyl groups, which is represented by the following formula (4):

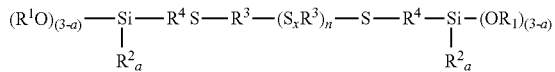

(4)

In this formula, $R^1$, $R^2$, $R^3$, "a", and "n" are the same as defined above. Furthermore, $R^4$ used in this formula is a residue which is formed due to an addition reaction between the aliphatic unsaturated bonds contained in $R^5$ of aforementioned formula (1) in component (A) and hydrogen atoms of mercapto groups in component (B). This residue may comprise a divalent hydrocarbon group with 2 to 16 carbon atoms. It is recommended that $R^4$ comprise an alkylene group with 2 to 16 carbon atoms, an aryl-substituted alkylene group with 8 to 16 carbon atoms, or a divalent organic group represented by the formula (5) given below with 5 to 16 carbon atoms:

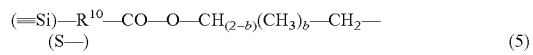

(5)

(where $\equiv$Si) and (S—) are, respectively, a silicon atom and a sulfur atom bonded to a divalent organic group; $R^{10}$ is an alkylene group with 1 to 12 carbon atoms, and "b" is 0 or 1). Of these, most preferable are the alkylene group and the organic group of formula (5), in particular, an ethylene group or a divalent organic group of the following formula: methylhydrogenpolysiloxanes endblocked by trimethylsiloxy at both terminals,

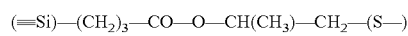

(where ($\equiv$Si) and (S—) are the same as defined above); "x" is an number, which on average is greater than 1 and smaller than 8 or equal to 8.

The silicon-containing polysulfide-type polymer, in particular, the polysulfide-type polymer that contains organosilyl groups obtained by the method of the present invention, may be used as a surface improving agent for inorganic powders such as silica, diatomaceous earth, or the like. It can be utilized as an additive to an inorganic filler, which is compounded with a vulcanizable rubber composition. The aforementioned additive can improve reinforcement properties of such a filler.

EXAMPLES

The invention will now be described with reference to practical examples.

Example 1

A 200 mL four-neck flask equipped with a reflux condenser and thermometer, was filled with the following components added in a flow of nitrogen gas: 30.5 g (0.21 mole) of vinyltrimethoxysilane ( a product of Dow Corning Toray Silicone Co., Ltd., product name: SZ6300); 100 g (0.10 mole) of diethoxymethane disulfide polymer having molecular terminals capped with mercapto groups, this polymer being expressed by formula (6) shown below and having an average molecular weight of 1000 and a viscosity of 1.2 Pa·s (a product of Toray Fine Chemical Co., Ltd.):

(6)

(where "n" is number which, on average, is 5);
32 g of sulfur powder (in an amount of 2.0 mole per 1 mole of repeating units contained in the mercapto-capped diethoxymethane disulfide polymer) (a product of Hosoi Chemical Industries Co., Ltd.); and 0.5 g (0.005 mole) of triethylamine (a product of Kanto Chemical Co., Ltd.). The components were mixed for 2 hours at 65° C., cooled to room temperature, and then non-reacted substance was removed by heating to 150° C. under a vacuum of 4 Torr. As a result, 158.6 g of a reddish-brown transparent liquid were obtained. The product was obtained with the yield of 97.6%. The obtained liquid was identified with IR, $^{13}$C-NMR, and $^{29}$Si-NMR as a polysulfide-type polymer that contains alkoxysilyl groups ("n" is on average equal to 5) and is expressed by the following formula (7):

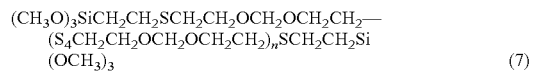

(7)

Example 2

A 200 mL four-neck flask equipped with a reflux condenser and thermometer, was filled with the following components added in a flow of nitrogen gas: 52.1 g (0.21 mole) of 3-methacryloxypropyl trimethoxysilane (a product of Dow Corning Toray Silicone Co., Ltd., product name: SZ6030); 100 g (0.10 mole) of diethoxymethane disulfide polymer having molecular terminals capped with mercapto groups, this polymer being expressed by aforementioned formula (6) and having an average molecular weight of 1000 and a viscosity of 1.2 Pa·s (a product of Toray Fine Chemical Co., Ltd.; 32 g of sulfur powder (in an amount of 2.0 mole per 1 mole of repeating units contained in the mercapto-capped diethoxymethane disulfide polymer) (a product of Hosoi Chemical Industries Co., Ltd.); and 0.5 g (0.005 mole) of triethylamine (a product of Kanto Chemical Co., Ltd.). The components were mixed for 2 hours at 95° C., cooled to room temperature, and then non-reacted substance was removed by heating to 150° C. under a vacuum of 4 Torr. As a result, 179.4 g of a reddish-brown transparent liquid were obtained. The product was obtained with the yield of 97.4%. The obtained liquid was identified with IR, $^{13}$C-NMR, and $^{29}$Si-NMR as a polysulfide-type polymer that contains alkoxysilyl groups ("n" is on average equal to 5) and is expressed by the following formula (8):

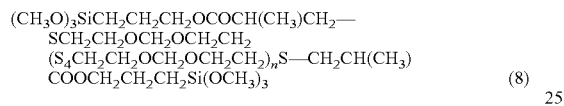

Example 3

A 200 mL four-neck flask equipped with a reflux condenser and thermometer, was filled with the following components added in a flow of nitrogen gas: 30.5 g (0.21 mole) of vinyltrimethoxysilane (a product of Dow Corning Toray Silicone Co., Ltd., product name: SZ6300); 100 g (0.10 mole) of diethoxymethane disulfide polymer having molecular terminals capped with mercapto groups, this polymer being expressed by aforementioned formula (6) and having an average molecular weight of 1000 and a viscosity of 1.2 Pa·s (a product of Toray Fine Chemical Co., Ltd.; 3.2 g of sulfur powder (in an amount of 0.2 mole per 1 mole of repeating units contained in the mercapto-capped diethoxymethane disulfide polymer) (a product of Hosoi Chemical Industries Co., Ltd.); and 0.5 g (0.005 mole) of triethylamine (a product of Kanto Chemical Co., Ltd.). The components were mixed for 2 hours at 65° C., cooled to room temperature, and then non-reacted substance was removed by heating to 150° C. under a vacuum of 4 Torr. As a result, 129.3 g of a reddish-brown transparent liquid were obtained. The product was obtained with the yield of 96.7%. The obtained liquid was identified with IR, $^{13}$C-NMR, and $^{29}$Si-NMR as a polysulfide-type polymer that contains alkoxysilyl groups ("n" is on average equal to 5) and is expressed by the following formula (9):

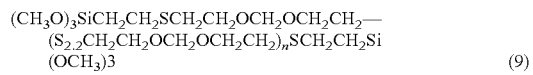

Comparative Example 1

The process was performed in the same manner as in Practical Example 1 with the exception that sulfur was not added; mixing was carried out at 65° C. during 5 hours. Identification of the product by IR analysis after completion of the mixing showed that the reaction did not occur.

Comparative Example 2

The process was performed in the same manner as in Practical Example 1 with the exception that the triethylamine was not added; mixing was carried out at 65° C. during 5 hours. Identification of the product by IR analysis after completion of the mixing showed that the reaction did not occur.

INDUSTRIAL APPLICATION

The method of the invention makes it possible to produce a silicon-containing polysulfide-type polymer, in particular, a polysulfide-type polymer that contains organosilyl groups, in an efficient and stable manner, in a single, simple, and low-temperature reaction process without generation of toxic gaseous hydrochlorides and hydrosulfide, without formation of halogen-containing salts and sulfur compounds that require the use of complicated waste-treatment processes, practically without formation of other by-products, and without a need in such additional processes as dehydration, removal of salts, hydrosulfides, etc. If preparation of the product is carried out in accordance with the method of the invention, it becomes possible to obtain a silicon-containing polysulfide-type polymer, in particular, a polysulfide-type polymer that contains organosilyl groups, without formation of residues, such as hydroxyl groups reactive with alkoxysilyl groups, and hence, with high storage stability.

The invention claimed is:
1. A method for the preparation of a reaction product consisting essentially of a silicon-containing polysulfide-type polymer having the following formula:

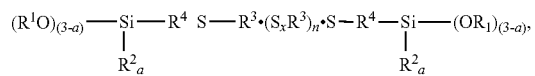

where $R^1$ is an alkoxyalkylene group or a monovalent hydrocarbon group with 1 to 10 carbon atoms; $R^2$ is a monovalent hydrocarbon group with 1-15 carbon atoms, other than monovalent hydrocarbon groups having an aliphatic unsaturated bond; $R^3$ is selected from an alkylene group with 2 to 10 carbon atoms, an arylene group with 6 to 10 carbon atoms, an alkylenoxyalkylene group with 2 to 10 carbon atoms, or a divalent organic group of formula:

where $R^8$ are the same or different alkylene groups with 1 to 10 carbon atoms, and "m" is an integer between 2 and 20, and a hydroxy-substituted alkylene group with 3 to 12 carbon atoms; $R^4$ is a residue formed in an addition reaction of the aliphatic unsaturated bond contained in component (A) given below to a hydrogen atom of the mercapto group of below-given component (B); "a" is an integer between 0 and 3; "x" is a number which on average is greater than 1 and smaller than 8 or equal to 8; and "n" is a number with a mean value between 1 and 120, said method characterized by simultaneously mixing (A) a silicon-containing compound having a silicon atom-bonded monovalent organic group with an aliphatic unsaturated bond; (B) a polysulfide polymer with at least two mercapto groups in one molecule; and (C) triethylamine used in an amount of 0.01 to 10 mole % relative to said component (A); said simultaneous mixing being carried out in the presence of (D) sulfur used in such an amount that sulfur atoms constitute 1 to 600 mole % relative to 1 mole of the repeating units ($S_xR^3$) in said silicon-containing polysulfide-type polymer.
2. The method of claim 1, wherein said component (A) is an organosilane having a silicon atom-bonded monovalent organic group having an aliphatic unsaturated bond, and wherein said silicon-containing polysulfide-type polymer is a polysulfide-type polymer that contains an organosilyl group.

3. The method of claim 2, wherein said organosilane contains a silicon atom-bonded monovalent organic group with an aliphatic unsaturated bond and a silicon atom-bonded alkoxy group.

4. The method of claim 1, wherein said component (A) is an organosilane or mixture of organosilanes represented by the following formula (1):

where $R^1$ is an alkoxyalkylene group or a monovalent hydrocarbon group with 1 to 10 carbon atoms, $R^2$ is a monovalent hydrocarbon group with 1-15 carbon atoms, other than monovalent hydrocarbon groups having an aliphatic unsaturated bond, $R^5$ is a monovalent hydrocarbon group with 2 to 16 carbon atoms having an aliphatic unsaturated bond, and "a" is an integer between 0 and 3.

5. The method of claim 1, wherein said component (B) is a polysulfide polymer having molecular terminals capped with mercapto groups, which is expressed by the following formula (2):

where $R^3$ is selected from an alkylene group with 2 to 10 carbon atoms, an arylene group with 6 to 10 carbon atoms, an alkylenoxyalkylene group with 2 to 10 carbon atoms, or a divalent organic group of formula (3):

where $R^8$ are the same or different alkylene groups with 1 to 10 carbon atoms, and "m" is an integer between 2 and 20, and a hydroxy-substituted alkylene group with 3 to 12 carbon atoms; "y" is a number with a mean value between 1.7 and 2, and "n" is a number with a mean value between 1 and 120.

6. The method of claim 1, wherein said simultaneous mixing of said components (A) to (D) is carried out at a temperature within a range from room temperature to 200° C.

7. The method of claim 5, wherein said simultaneous mixing of said components (A) to (D) is carried out in an atmosphere of inert gas.

8. A method for the preparation of a reaction product consisting essentially of a polysulfide-type polymer having an organosilyl group represented by the following formula (4):

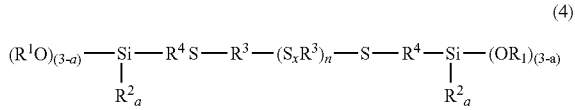

wherein $R^1$, $R^2$, $R^3$, "a" and "n" are the same as defined below, $R^4$ is a residue formed in an addition reaction of the aliphatic unsaturated bond contained in below-defined $R^5$ of formula (1) of component (A) given below to a hydrogen atom of the mercapto group of below-given component (B), and "x" is a number which on average is greater than 1 and smaller than 8 or equal to 8, said method characterized by simultaneously mixing:

(A) an organosilane or mixture of organosilanes represented by the following formula (1):

where $R^1$ is an alkoxyalkylene group or a monovalent hydrocarbon group with 1 to 10 carbon atoms, $R^2$ is a monovalent hydrocarbon group with 1-15 carbon atoms, other than monovalent hydrocarbon groups having an aliphatic unsaturated bond, $R^5$ is a monovalent hydrocarbon group with 2 to 16 carbon atoms having aliphatic unsaturated bonds, and "a" is an integer between 0 and 3;

(B) a polysulfide polymer having molecular terminals capped with mercapto groups, which is expressed by the following formula (2):

where $R^3$ is selected from an alkylene group with 2 to 10 carbon atoms, an arylene group with 6 to 10 carbon atoms, an alkylenoxyalkylene group with 2 to 10 carbon atoms, or a divalent organic group of formula (3):

where $R^8$ are the same or different alkylene groups with 1 to 10 carbon atoms, and "m" is an integer between 2 and 20, and a hydroxy-substituted alkylene group with 3 to 12 carbon atoms; "y" is a number with a mean value between 1.7 and 2, and "n" is a number with a mean value between 1 and 120, said component (B) being used in an amount of 10 to 200 mole % relative to said component (A);

(C) triethylamine used in an amount of 0.01 to 10 mole % relative to said component (A); and (D) sulfur used in such an amount that sulfur atoms constitute 1 to 600 mole % relative to 1 mole of the repeating units $(S_yR^3)$ in said component (B).

9. The method for the preparation of a polysulfide-type polymer having an organosilyl group according to claim 8, wherein said simultaneous mixing is carried out in an atmosphere of inert gas at a temperature within a range from room temperature to 95 ° C.

10. The method of claim 1, wherein said simultaneous mixing is carried out in an atmosphere of inert gas at a temperature within a range from 60 to 95 ° C.

11. The method for the preparation of a polysulfide-type polymer having an organosilyl group according to claim 8, wherein said simultaneous mixing is carried out in an atmosphere of inert gas at a temperature within a range from 60 to 95 ° C.

12. The method of claim 1, further comprising the step of heating in vacuum the reaction product to obtain the silicon-containing polysulfide-type polymer.

13. The method for the preparation of a polysulfide-type polymer having an organosilyl group according to claim 8, further comprising the step of heating in vacuum the reaction product to obtain the polysulfide-type polymer having an organosilyl group.

* * * * *